United States Patent [19]
Schugt

[11] Patent Number: 5,922,958
[45] Date of Patent: Jul. 13, 1999

[54] ACOUSTIC CHANNEL FOR CONTAMINANT DETECTION ON A SURFACE

[75] Inventor: Michael A. Schugt, Minneapolis, Minn.

[73] Assignee: Rosemount Aerospace Inc., Burnsville, Minn.

[21] Appl. No.: 08/651,638

[22] Filed: May 22, 1996

[51] Int. Cl.[6] .................................................. G01N 29/22
[52] U.S. Cl. .......................................... 73/596; 73/170.26
[58] Field of Search ................................ 73/170.26, 596, 73/597; 340/580, 582, 962, 583; 244/134 F

[56] References Cited

U.S. PATENT DOCUMENTS

| | | | |
|---|---|---|---|
| 4,404,852 | 9/1983 | Goto | 340/582 |
| 4,461,178 | 7/1984 | Chamuel | 340/582 |
| 4,604,612 | 8/1986 | Watkins | 340/582 |
| 5,456,114 | 10/1995 | Lui | 73/597 |

*Primary Examiner*—Christine K. Oda
*Attorney, Agent, or Firm*—Westman, Champlin & Kelly, P.A.

[57] ABSTRACT

A sensor plate is formed as an acoustic channel on which an acoustic transducer is mounted to send ultrasonic waves along a surface of a base wall of the acoustic channel which is exposed to contaminants to be detected. An insert plate encloses the channel to protect the surface opposite the surface exposed to contaminants from the environment. Thus, dirt, moisture, installation adhesives or other materials that might degrade the performance of the sensor are prevented from contacting the backside of the plate carrying the acoustic waves. Such acoustic channel sensors are useful in applications on aircraft surfaces, road surfaces, bridge surfaces and the like for detecting ice.

13 Claims, 6 Drawing Sheets

ACOUSTIC CHANNEL FOR CONTAMINANT DETECTION ON A SURFACE

This invention was made with Government support under Agreement No. MDA 972-94-3-0044 awarded by the Advanced Research Projects Agency. The Government has certain rights in the invention.

BACKGROUND OF THE INVENTION

The present invention relates to sensor plates forming an acoustic channel vibrated with ultrasonic energy, and which can be used for detection of contaminants, such as ice on a surface on the plate.

Detection of contaminants on surfaces, such as ice on the wings of an aircraft, has generally been done with various types of probes or sensors that detect the ice only at specific locations. Two types of ice detectors are shown in U.S. Pat. Nos. 4,980,673, and 3,277,459. U.S. Pat. No. 4,980,673 discloses a magnetostrictive resonance damping sensor while U.S. Pat. No. 3,277,459 shows a sensor which works on sensing heat of transformation.

In addition, mechanical scrapers have been used for measuring ice build up by scraping a target and determining the ice removal. The change in optical index of refraction of a surface has been used for determining when a surface has become coated with ice, by comparing the measured index to the index when the surface was uncoated. Other types of sensors used for ice detection include radiation absorption detectors, capacitive ice detectors, conductivity ice detectors, the damping of piezoelectric vibrating elements, and resonance damping of magnetostrictive elements. A vibrating ice detector that utilizes a non intrusive surface is illustrated in U.S. Pat. No. 4,611,492.

Most of the ice detectors described above detect ice at a single point, while accumulation in different portions of a surface can go undetected. Further, the sensors generally are spaced from wing surfaces of the aircraft. Most sensors also significantly increase drag and weight.

SUMMARY OF THE INVENTION

The present invention relates to a thin plate acoustic sensor formed into an acoustic channel which conforms to a surface on which it attaches, such as on an aircraft wing upper surface or leading edge. The acoustic channel is used for detecting ice and other contaminant accumulation across a relatively large area defined by the sensor plate size. The channel that is formed in the plate has a relatively thin base wall having an outer surface exposed to the environment that is monitored for icing conditions.

The inner surface of the base wall of the acoustic channel faces toward the surface on which the thin plate sensor is mounted. An acoustic transducer is mounted on the plate and is energized to send an ultrasonic (acoustic) wave along a sensor surface exposed to the environment being monitored, and the wave or pulse is sensed by a transducer either at the opposite end of the plate, or as shown, at the same end of the plate after the ultrasonic wave has been reflected back. Commercially available transducers for transmitting and receiving such ultrasonic pulses are utilized. The frequency of the wave carried by the sensor plate changes if ice or other contaminants are deposited on the exposed surface.

The transmitting transducer is positioned to preferably send a "lamb" wave, which is a vibration transmitted along the exposed surface. The transmitter transducer can also be used for transmitting compression waves. The acoustic channel is sensitive to any contaminant that adheres to the surface but yet will be somewhat insensitive to materials where there is no substantial shear transmission between the contaminant and the surface, such as with water on the surface.

The transducer used for both transmitting and receiving signals is preferably a known piezoelectric type vibrating element that will transmit or receive high frequency waves. A separate transmitting transducer and a separate receiving transducer may be used.

The acoustic channel provides for very sensitive detection of actual ice formation within a substantial area of critical flight surfaces.

The present invention insures that the surface of the plate sensor opposite from the exposed surface is not subjected to contaminants that will affect the frequency of the ultrasonic pulse transmission. The underside of the sensor plate in ordinary plate sensors is subject to picking up water, dust or the like, which adversely affects the sensor accuracy and reliability. The present invention keeps the underside of the sensor plate free of any and all extraneous contaminants such as moisture, to reduce errors in the data received.

The present invention comprises a filler plate that is within the acoustic channel and sealed around the edges of the channel. The filler plate is acoustically decoupled from the bottom surface of the base wall of the channel that is transmitting the acoustic energy.

The filler plate is bonded such as by brazing or adhesives or welding, around its periphery to completely enclose the channel. The vibrating acoustic channel base wall is not dampened with the protective filler plate. A small spacing between the base wall of the channel and the filler plate insures that the filler plate will not degrade the acoustic signal.

DETAILED DESCRIPTION OF THE PREFERRED EMBODIMENTS

Figure 1:
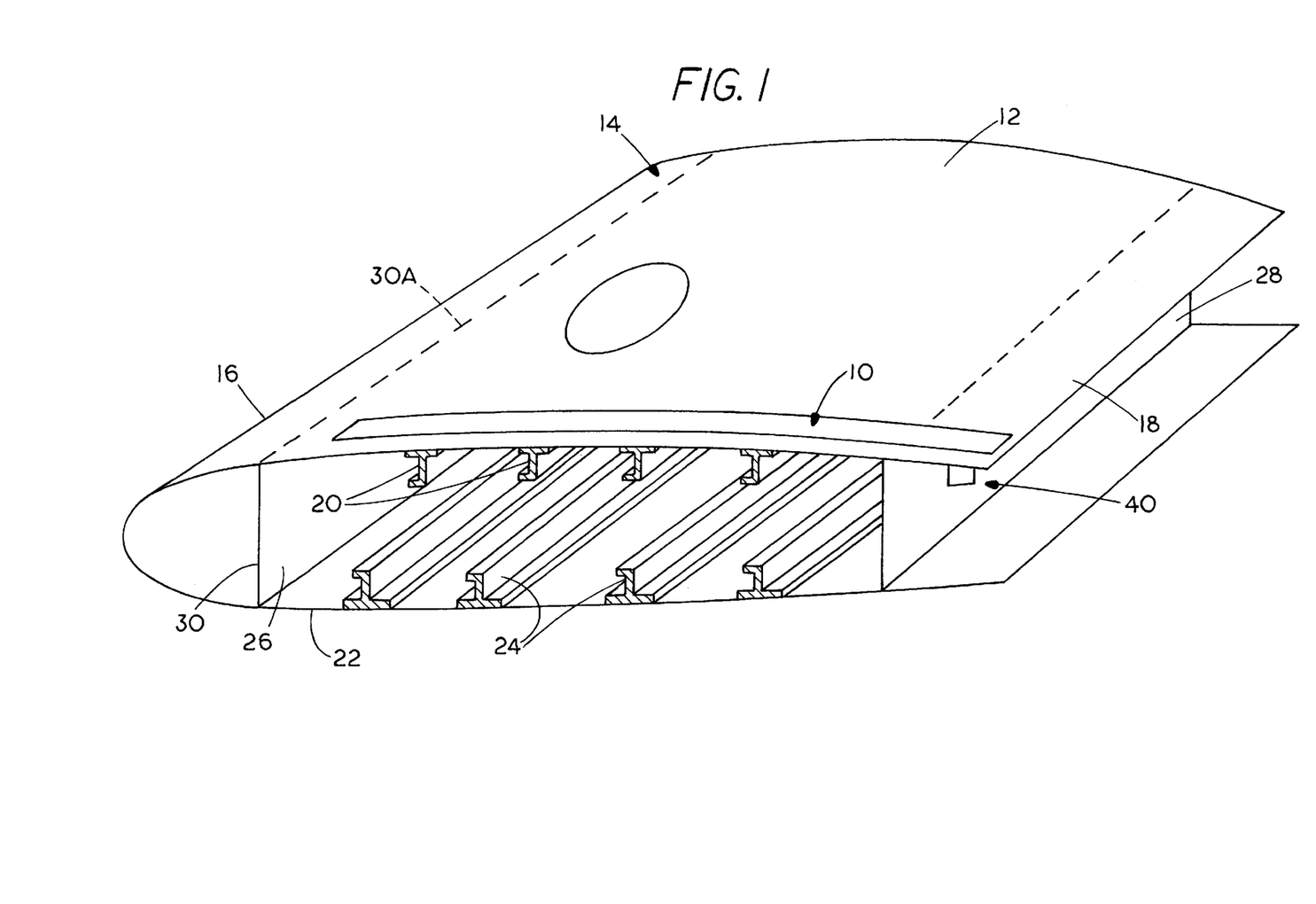
FIG. 1 is a perspective view of a typical contaminant plate sensor made according to the present invention, shown installed on the wing of an aircraft.

Referring to FIG. 1, an acoustic plate contaminant sensor 10 is shown schematically in position extending along the upper skin layer 12 of an aircraft wing 14. As shown the plate sensor 10 extends essentially in the direction of airflow across the wing from a leading edge 16 to a trailing edge portion 18 that is shown only schematically.

The upper aircraft skin 12 is stiffened with suitable structural members 20, and the lower skin 22 is stiffened with structural members 24 that extend along the length of the wing. The interior space in which the structural members extend generally forms a fuel tank space indicated at 26. A rear spar dividing wall 28 and a front dividing wall 30 are used for defining the tank. This means that the trailing wing portion 18 is an open area, and provides space for transducers, as long as the transducers do not protrude into the area where wing flaps operate.

Figure 2:
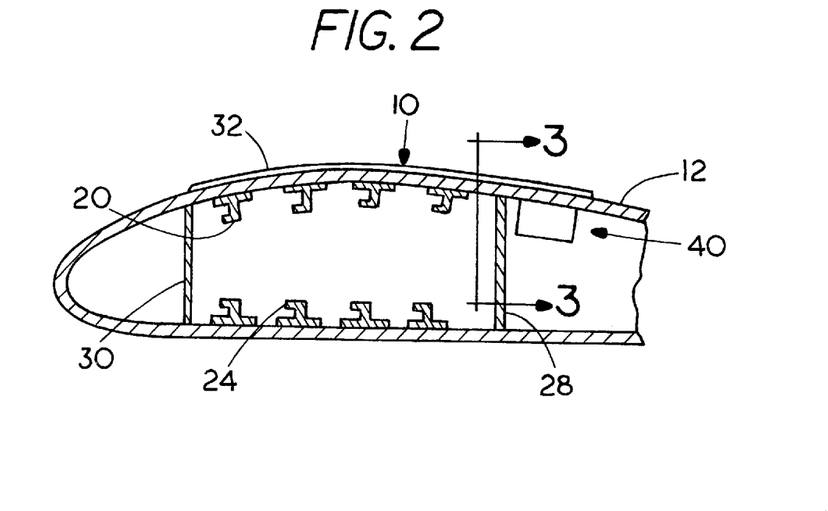
FIG. 2 is a sectional view of a wing, illustrating the general configuration of the sensor installation, and the positioning of one form of the transducers utilized.
Figure 3:
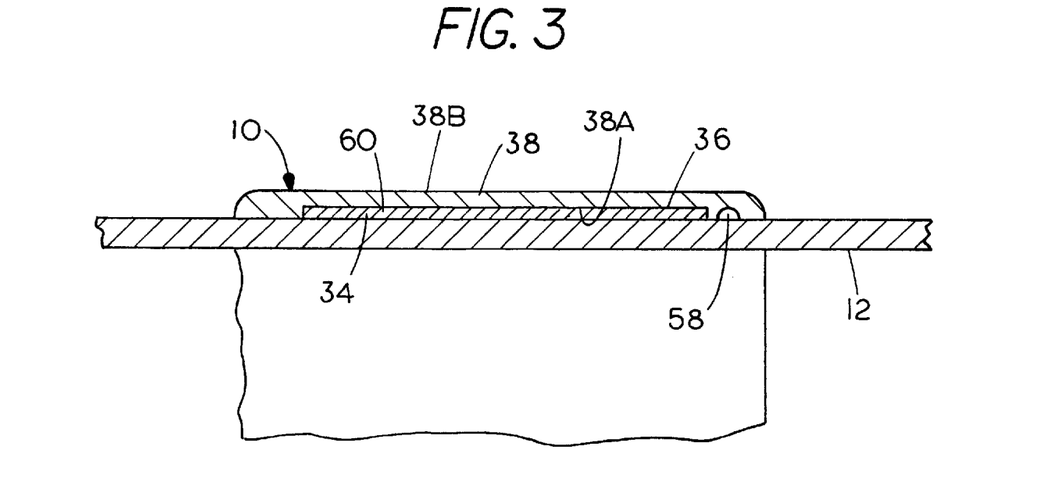
FIG. 3 is a sectional view taken along line 3—3 in FIG. 2.

The acoustic plate sensor 10 as shown in FIG. 2 comprises a plate of metal 32 that has a length that is positioned parallel to the chord of the wing 14 as shown, and it is fastened in place with suitable fasteners such as flush rivets or by bonding. The plate has a longitudinally extending, generally rectangular recess 34 (see FIGS. 3 and 4), which runs along a substantial portion of the length of the plate 32. The recess 34 is bounded by a flange 33 that is used for mounting the plate 32 onto an aircraft skin. Recess 34 forms an acoustic channel 36 that is formed into the plate 32 to provide a very thin channel base wall 38, which, when installed, has an interior surface 38A, and an exterior surface 38B. The wall 38 forms the base of the acoustic channel 36, as defined by the recess 34.

Figure 4:
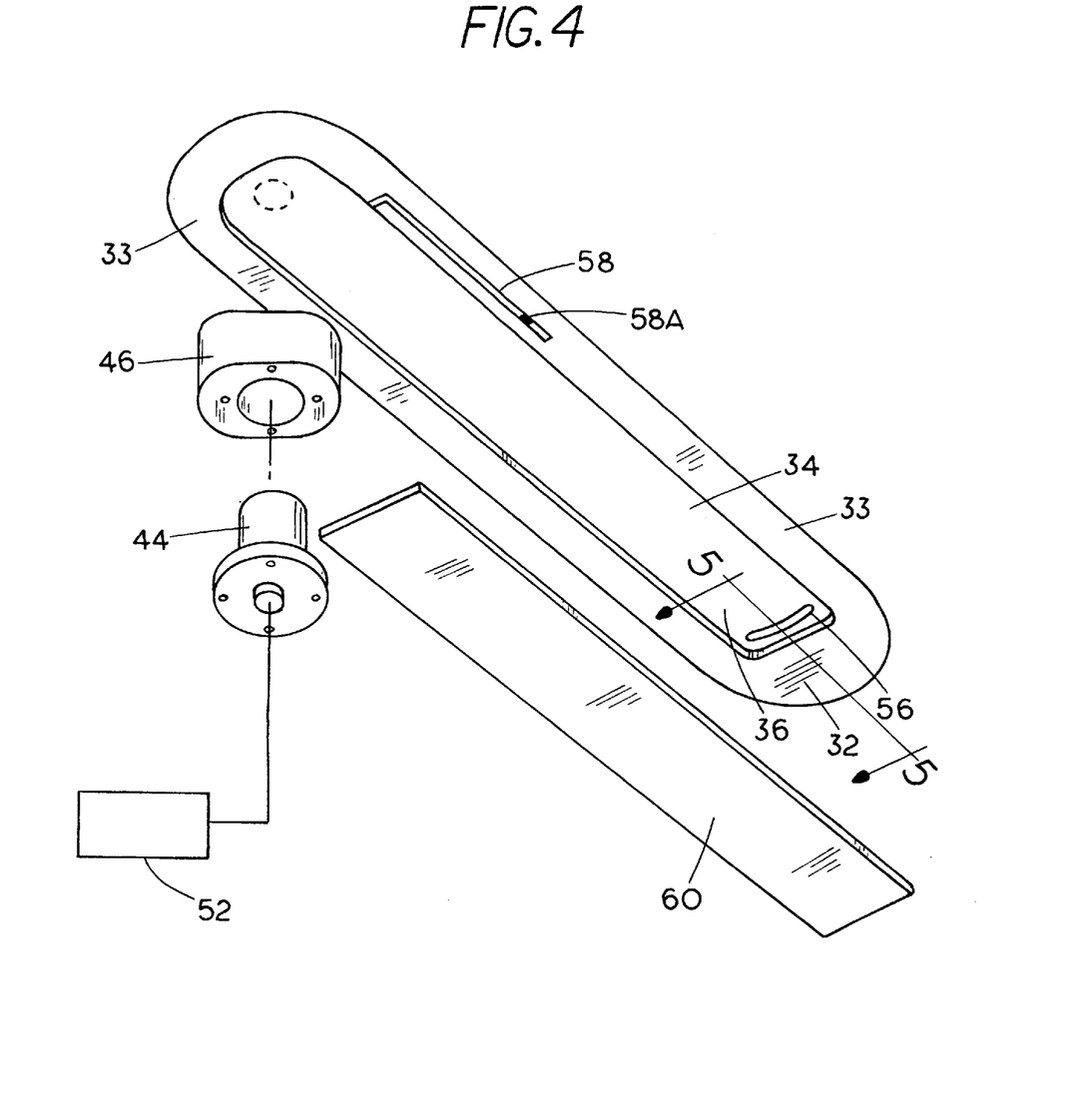
FIG. 4 is an exploded view of the underside of the sensor shown in FIG. 1.
Figure 8:
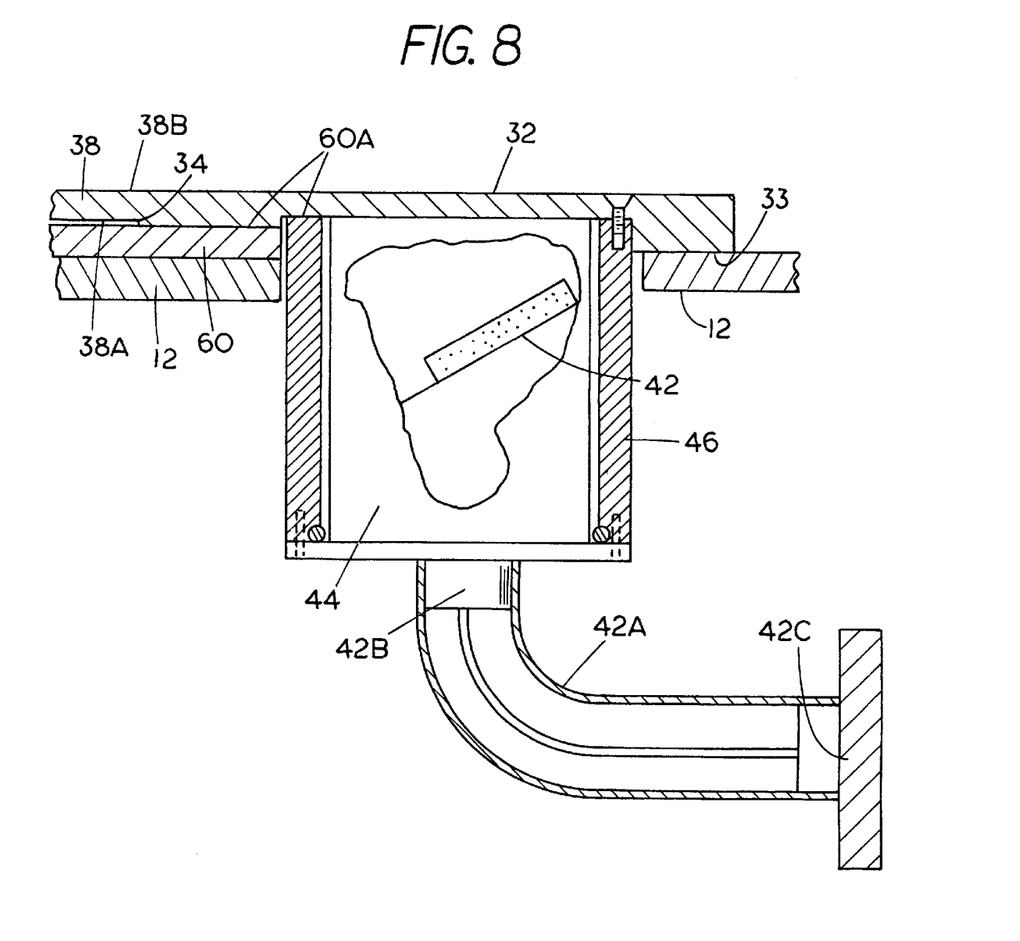
FIG. 8 is a schematic sectional view through a transducer mounting frame showing a typical transducer in position on a plate sensor.

The ultrasonic energy to cause vibration in the sensor 10 is provided by a transducer assembly 40, which is shown in exploded form in FIG. 4, and also is shown in a typical sectional view in FIG. 8. The acoustic transducer used is preferably a well known piezoelectric sensor element that when energized will vibrate at selected frequencies. The sensor element will also receive vibrations and will provide an output electrical signal indicating, e.g. the frequency of the received acoustic vibration. The techniques of transmitting and receiving vibrations is well known.

In the form shown, as generally illustrated in FIG. 4, there is one transducer 42 that is mounted in a housing 44. The transducer is positioned so that the plane of the piezoelectric element that sends and receives the acoustic energy is at an angle relative to the general plane of the acoustic channel wall 38, to achieve a desired acoustic wave form (lamb wave) on the outer surface 38B of the wall 38.

The transducer housing 44 is in turn mounted in a suitable transducer support 46, that has a receptacle for the transducer housing, and will permit removably mounting the transducer housing 44. The position of the transducer support 46 on the plate 32, within the channel is shown in dotted lines in FIG. 4. The transducer support 46 is fastened securely on the interior surface 38A of the wall 38 of the acoustic channel 36 in sensor plate 32, at one end of the recess 34. The transducer assembly 40 extends through an opening provided through the wing skin 12, and into an open area below the skin as shown in FIGS. 1 and 2. Alternatively, the sensor assembly 10 can be placed where the transducer assembly 40 protrudes into the fuel tank in the aircraft wing, but extra care has to be taken then for sealing the transducer assembly and for making sure that there is no likelihood of leaks or of contamination of the fuel.

A suitable circuit or circuits 52 of known design can be connected to the transducer 42 respectively, for providing excitation for the transducer to create an acoustic wave during a first time period, and for receiving and processing a return signal (typically a frequency signal) during a second time period, in a known manner. The transmission and reception time periods cycle while the sensor 10 is operating. Thus the circuit forms part of a means for determining changes in the reflected or return acoustic vibration. A separate transducer also can be used for such detection of return signals. As shown schematically in FIG. 8, a braided shield 42A is mounted to a transducer connector 42B and is rounded to the airframe 42C for lightning protection.

Figure 5:
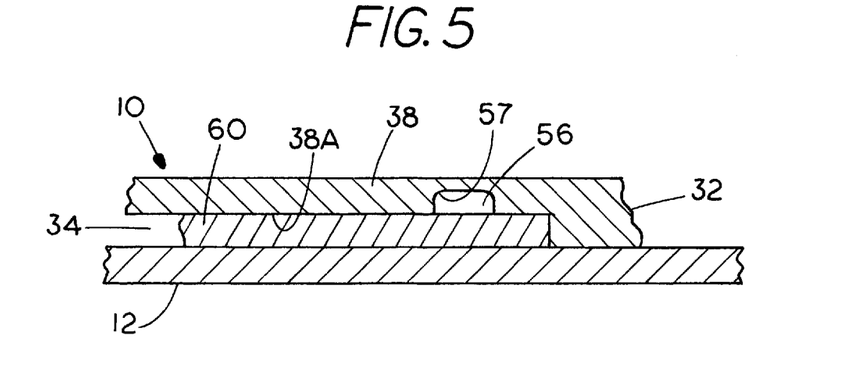
FIG. 5 is a fragmentary enlarged sectional view taken along 5—5 in FIG. 4.

The plate 32, in the form shown, has one acoustic pulse or signal generating transducer which also receives the echo signal at one end of the channel. A groove 56 is formed in wall 38 at the opposite end of the channel from the transducer. The groove 56 forms a wave reflecting surface for the acoustic signal to be echoed back to the sensor assembly 40 for sensing by the transducer 42. The interior corner 57 of the groove (see FIG. 5) is rounded as shown to reduce bounce of the acoustic signals. The amount of rounding can vary, depending on the frequency of the transmitted acoustic signal.

Since the inner transducer support 46 is secured directly to the interior surface 38A of wall 38 on the interior of the acoustic channel 36 formed by recess 34, the acoustic vibrations from transducer 42 are transmitted directly to the wall 38.

The plate 32 is provided with a groove indicated at 58 along one side of the acoustic channel 36 for receiving a temperature sensor 58A which measures the actual temperature of the sensor assembly 10. Knowing the temperature aids in interpreting changes in the acoustic frequency. The operator can tell when the unit is near freezing temperature.

The groove 56, which forms a reflection surface, has a longitudinal arcuate shape, with the center of the arc being centered on the transducer 42 so that the reflections of the acoustic waves will be focused back toward the transducer rather than scattered.

The present invention includes the use of a protective insert cover plate 60 filling the recess 34. Plate 60 is adjacent to and may appear to touch interior surface 38A, of wall 38 but it is acoustically decoupled from that surface 38A. The insert cover plate 60 is hermetically sealed to the sensor plate 32, around the entire periphery of the recess 34. This hermetic sealing is carried out by brazing, welding, or the sealing of plate 60 can be done by using a suitable non deteriorating adhesive, particularly for industrial or non-aircraft uses. The end of the plate 60 adjacent the housing 48 for the transducer 42 is sealed to the underside edge of the housing 48.

The insert cover plate 60 will not substantially attenuate the acoustic energy being transmitted along the wall 38, since at least a molecular layer of air spaces the interior surface 38A of wall 38 and the plate 60, although the cover plate is secured to plate 32 at its edges. Insert cover plate 60 insures that contaminants will not lodge on the interior surface 38A which would cause false signals from items that are not directly contaminating the exterior surface 38B and the exterior surface of the aircraft skin.

Protective insert cover plate 60 can be made of any suitable metallic material, and is generally of the same type of material as the plate 32, such as aluminum or an alloy thereof.

The flange 33 of the plate 32 surrounding the recess 34 can then be secured to the wing surface in a suitable manner using existing wing hardware or bonding it in place to minimize drag.

The recess 34 in sensor plate 32 can be formed by any suitable known manner of milling or machining, or other types of known processes for forming channels in relatively thin plates. The plate is formed as thin as possible, and as large as reasonable. The power needed to drive the transducer sufficiently increases as the size of the plate increases.

It should be noted that since the transducer support 46 extends into recess 34 of plate 32 and seats on the interior surface 38A, the protective insert plate 60 will abut the sidewall of the transducer support. A hermetic seal, such as a brazed joint, between the sidewall of the transducer support 46, and the abutting edge of plate 60 indicated at 60A is formed so that a very tight seal is maintained along all edges of the plate 60.

The transducer 42 has an internal piezoelectric element that has a plane positioned at a selected angle relative to the general plane of the sensor plate 32, as shown in FIG. 8, and by selecting the appropriate frequency, which can be determined analytically by knowing the configuration of the acoustic channel formed in plate 32, a "lamb wave" can be generated in wall 38. This means that the acoustic wave will be transmitted right along the exterior surface 38B exposed to contaminants and will be reflected by a surface of slot 56 back along interior surface 38A as well. The frequency of acoustic vibration is selected to match the geometry of the sensor plate 32. Making wall 38 as thin as possible is desirable. Wall 38 as desired is slightly less thick than the depth of the recess 34 and protective insert plate 60. Establishing a frequency of vibration where water on the exterior surface 38B of wall 38 acts differently than ice is desirable.

Figure 6:
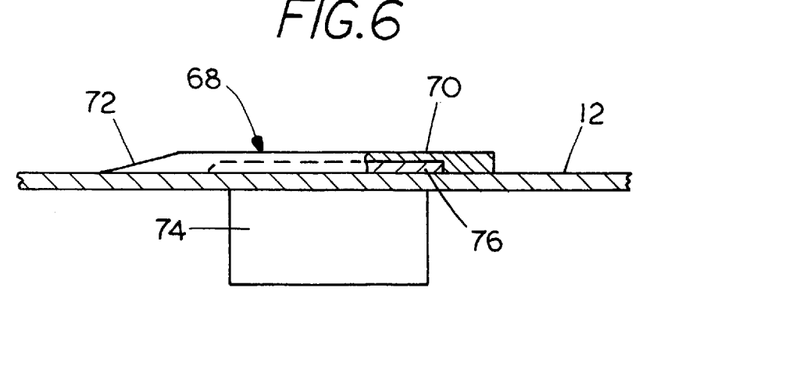
FIG. 6 is a schematic representation of an installation extending along a leading edge of the wing, showing a tapered leading end of the plate sensor.

FIG. 6 shows an alternative method of mounting an acoustic sensor assembly. The plate sensor assembly 68 is mounted parallel to and adjacent the leading edge of the wing on top of the aircraft skin 12. For example, the sensor assembly 68 may be positioned to extend just forwardly of the wall 30 or to the rear of spar dividing wall 28, shown in FIGS. 1 and 2 and extend along the dotted line 30A that is illustrated in FIG. 1. FIG. 6, a cross sectional view shows that the sensor assembly 68 includes a sensor plate 70 that had a tapered leading edge 72 to minimize drag, and provide for smooth air flow over the skin 12. A piezoelectric transducer assembly 74 is mounted at one end of the sensor assembly 68. The sensor plate 70 has a sealed protective insert cover plate 76 that would prevent contaminants from adhering to the under surface of the base wall of an acoustic channel formed in sensor plate 70. The sensor assembly 68 operates as previously explained.

Figure 7:
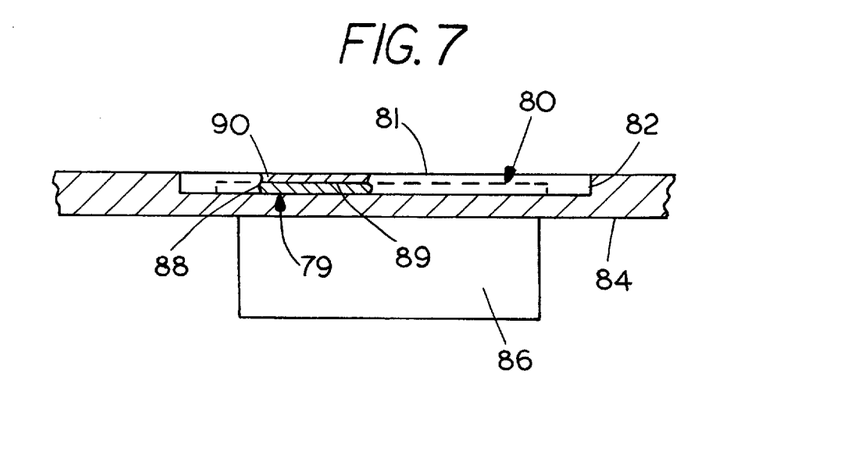
FIG. 7 is a sectional view similar to FIG. 6 illustrating a flush mounted acoustic plate sensor that fits into and is fastened in a recess formed in the aircraft skin.

As shown in FIG. 7, an acoustic sensor assembly 80 having acoustic channel 79 formed in a plate 81 can be positioned within a recess 82 in an aircraft skin 84 so that it has a flush outer surface with the aircraft skin, as illustrated. A transducer 86 would again be utilized as previously explained and extends through the aircraft skin 12 into the wing interior. A sealed protective insert cover plate 88 protects the under surface 89 of the base wall 90 of the acoustic channel 79 formed in plate 81. The assembly 80 is affixed to the wing skin 12 in any desired manner.

Figure 9:
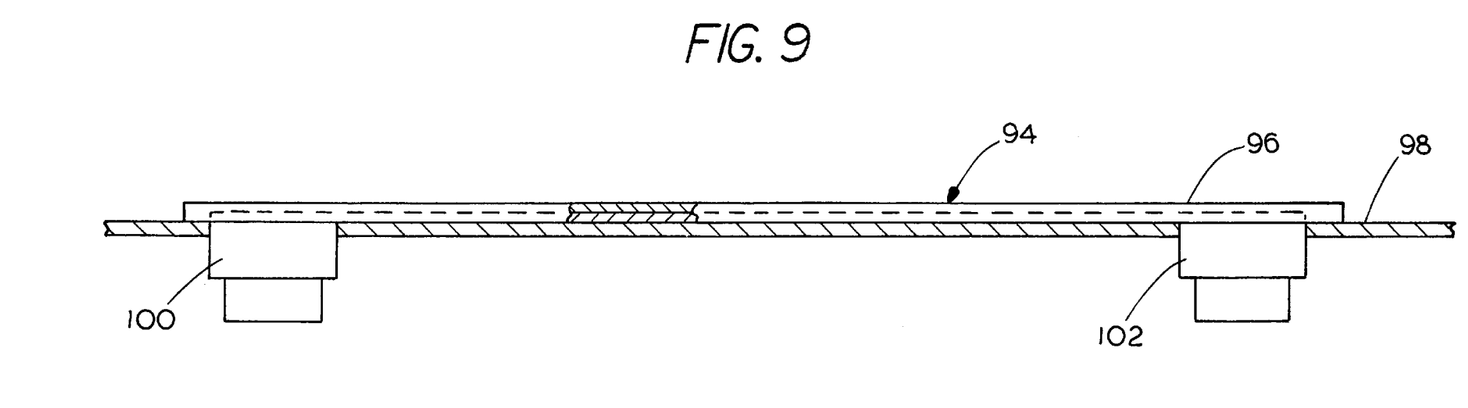
FIG. 9 is a schematic representation of a modified form of the invention utilizing a "pitch/catch" arrangement of transducers.

FIG. 9 illustrates a modified form of an acoustic transmission plate sensor assembly 94 that has a plate 96 (formed in the same manner as plate 32 of FIG. 2) and mounted onto an aircraft skin 98. In this form an acoustic signal transmitting transducer 100 is positioned at one end of the plate 94, and an acoustic signal receiving transducer 102 is positioned at the other end. This is a "pitch/catch" type sensor, and it is a modified form of the invention that would again utilize the sealing protective insert plate for enclosing the channel recess and preventing contaminants from adhering to the underside surface of the base wall of the channel formed in plate 94. The circuit 52 can be used for controlling these transducers as well, with suitable modification.

Other forms of acoustic transducers and transducer arrangements can also be utilized. In particular, it is known that in place of having the outer housing shown in FIG. 8 having an angled recess for receiving the transducer assembly, a block of suitable material can be placed at the end of the transducer to establish the appropriate angle, relative to the surface of the base wall of the acoustic channel and then the block and transducer mounted in a recess or bore that has a central axis perpendicular to the base wall of the acoustic channel and aircraft skin.

The present invention finds use in applications other than aircraft, for example, it can be used on bridges, roads, power lines, runways and similar locations where detection of ice and other unwanted contaminants that will affect the transmission characteristics of acoustic waves is important.

The disclosed preferred embodiment shows a single transducer for transmitting and receiving acoustic vibrations in a time sequence controlled in the circuit 52.

Although the present invention has been described with reference to preferred embodiments, workers skilled in the art will recognize that changes may be made in form and detail without departing from the spirit and scope of the invention.

What is claimed is:

1. An acoustic sensor comprising a sensor plate, a recess in the sensor plate forming an acoustic channel, a transducer assembly coupled to the sensor plate having means for providing an acoustic energy pulse forming an acoustic wave transmitted along a wall of the channel, the wall of the channel having a first surface exposed to conditions to be sensed, the transducer assembly including means for determining changes in the acoustic wave transmitted along the wall as a result of materials on the exposed surface, and a protective insert plate covering the recess forming the acoustic channel and being hermetically sealed around the periphery of the recess forming the acoustic channel.

2. The sensor of claim 1, wherein the transducer assembly portion providing the acoustic pulse is oriented to provide a lamb wave on the exposed surface of the wall of the acoustic channel.

3. The sensor of claim 1, wherein the transducer assembly is positioned at a first end of the acoustic channel, and the acoustic channel has a reflecting surface at a second opposite end thereof for reflecting acoustic waves transmitted from the means for providing an acoustic energy pulse.

4. The sensor of claim 1, wherein said means for providing an acoustic energy pulse is mounted at a first end of the acoustic channel and comprises an acoustic energy transmitter, and the means for determining changes in the acoustic wave comprises an acoustic energy frequency detector at an opposite end of the acoustic channel.

5. The sensor of claim 3, wherein the reflecting surface comprises a groove in the wall of the acoustic channel.

6. The sensor of claim 5, wherein the channel has a longitudinal length and the groove extends transverse to the longitudinal length.

7. The sensor of claim 6, wherein the groove has a rounded inner corner between a sidewall spaced farthest from the first end and a bottom wall to reduce bouncing of acoustic vibration carried by the wall of the acoustic channel.

8. The sensor of claim 1, wherein the sensor plate is mounted on a wing of an aircraft and extends parallel to a chord of the wing.

9. The sensor of claim 1, wherein the sensor plate is mounted on a leading edge of a wing of an aircraft.

10. The sensor of claim 1, wherein the insert plate is brazed to the edges of the recess of the sensor plate.

11. The sensor of claim 10, wherein the recess forms a channel base wall in the sensor plate that has a thickness less than the depth of the recess.

12. An acoustic sensor comprising a sensor plate, a recess in the sensor plate forming an acoustic channel having a length substantially greater than its width and with the recess forming a thin base wall of the channel, a transducer assembly coupled to the sensor plate having a first transducer portion for providing an acoustic energy pulse forming an acoustic wave transmitted along the base wall of the channel, the base wall of the channel having a surface exposed to conditions to be sensed, the transducer assembly including means for determining changes in frequency of the acoustic wave transmitted along the base wall of the channel as a result of materials on the exposed surface, and a protective insert plate within the recess forming the acoustic channel and being hermetically sealed around the periphery of the recess forming the acoustic channel to prevent contaminants from engaging a second surface of the base wall of the channel opposite from the first surface, said protective insert plate being acoustically decoupled from the second surface of the base wall of the channel.

13. The sensor of claim 12, wherein the transducer assembly is positioned at one end of the acoustic channel, and the acoustic channel having a reflecting surface at an opposite end thereof for reflecting acoustic waves transmitted from the means for providing an acoustic energy pulse, the reflecting surface comprising a groove formed partially through the base wall of the channel.

* * * * *